US00PP07836P

United States Patent [19]

Moser

[11] Patent Number: Plant 7,836

[45] Date of Patent: Mar. 24, 1992

[54] HIBISCUS PLANT NAMED CRIMSON TIDE

[75] Inventor: Frank C. Moser, Alva, Fla.

[73] Assignee: Yoder Brothers, Inc., Barberton, Ohio

[21] Appl. No.: 578,772

[22] Filed: Sep. 7, 1990

[51] Int. Cl.[5] ..... A01H 5/00

[52] U.S. Cl. ..... Plt./54

[58] Field of Search ..... Plt./54, 68, 67.8

*Primary Examiner*—Howard J. Locker

*Attorney, Agent, or Firm*—Foley & Lardner

[57] ABSTRACT

An Hibiscus plant named Crimson Tide particularly characterized by its vivid red flower color with a satin glow and dark red eye; regular single flower form; flower diameter of 130 to 150 mm; excellent pot habit with vigorous growth, good branching and very uniform performance; high production of flowers; flower life of a single day; easy to propagate; good resistance to Bacterial Leaf Spot, and good shipping tolerance.

2 Drawing Sheets

The present invention comprises a new and distinct cultivar of Hibiscus, botanically known as *Hibiscus rosasinensis* L., and referred to by the cultivar name Crimson Tide.

Crimson Tide, identified as 86-280005, was originated from a cross made by Frank C. Moser in a controlled breeding program in Alva, Fla., in 1985.

The female parent of Crimson Tide was the cultivar identified as Weismoor Sun, an unpatented Hibiscus cultivar with single flower form, an orange-red flower color, and a dark red eye.

The male parent of Crimson Tide was an unnamed seedling identified as 83-047001.

Crimson Tide was discovered and selected as one flowering plant within the progeny of the stated cross by Frank C. Moser in June 1986, in ground beds in Alva, Fla.

The first act of asexual reproduction of Crimson Tide was accomplished when vegetative cuttings were taken from the initial selection in November 1986 in ground beds in Alva, Fla., by technicians working under the supervision of Frank C. Moser.

Horticultural examination of controlled flowerings of successive plantings has shown that the unique combination of characteristics as herein disclosed for Crimson Tide are firmly fixed and are retained through successive generations of asexual reproduction.

Crimson Tide has not been observed under all possible environmental conditions. The phenotype may vary significantly with variations in environment such as temperature and light intensity.

The following observations, measurements and comparisons describe plants grown in Alva, Fla. under greenhouse conditions which approximate those generally used in Florida for commercial potted Hibiscus production.

The following traits have been repeatedly observed and are determined to be basic characteristics of Crimson Tide, which, in combination, distinguish this Hibiscus as a new and distinct cultivar:

1. Vivid red flower color with a satin glow.
2. Regular single flower form, with diameter of 130 to 150 mm.
3. Excellent pot habit with vigorous growth, good branching and very uniform performance.
4. High production of flowers.
5. Flower life of a single day.

6. Easy to propagate.
7. Good resistance to Bacterial Leaf Spot (Pseudomonas sp.)
8. Good shipping tolerance (bud drop resistance).

The accompanying photographic drawings show typical plant habit, flower and leaf characteristics of Crimson Tide, with the colors being as nearly true as possible with illustrations of this type.

Sheet 1 is a color photograph of Crimson Tide grown as a commercially finished pot plant, with 4 cuttings in a 15 cm. pot.

Sheet 2 is a black and white photograph of the foliage of Crimson Tide, ranging from small or immature to relatively large and mature.

Of the commercial cultivars known to the inventor, the most similar in comparison to Crimson Tide is the cultivar Brilliant Red, an unpatented cultivar. Crimson Tide has a brighter red flower color, a more uniform performance, and a higher production of flowers when compared with Brilliant Red. In addition, Crimson Tide has much better shipping tolerance (bud drop resistance) than Brilliant Red, and is much more resistant to Bacterial Leaf Spot than Brilliant Red, which is very susceptible. It is worth noting that bud drop in shipping budded plants has been a severe problem in many cultivars currently being grown. Breeding for varieties not showing this trait is a high priority breeding objective. Therefore, the trait of bud drop resistance in Crimson Tide is very important. Resistance to Pseudomonas sp. (Bacterial Leaf Spot) is also a very important trait. Cultivars which are very susceptible to this disease cannot be grown successfully in the Florida environment.

In the following description color references are made to The Royal Horticultural Society Colour Chart. The color values were determined on May 18, 1990 in Salinas, Calif. on plant material grown in Alva, Fla. and shipped as a budded plant to Salinas, Calif., where it was flowered. The very bright red color with satin glow of Crimson Tide is not represented in the R.H.S. Colour Chart, and the values given are those believed to be closest to the actual color of Crimson Tide.

Classification:

*Botanical.*—*Hibiscus rosasinensis* L. cv Crimson Tide.

*Commercial.*—Greenhouse pot Hibiscus.

INFLORESCENCE

A. Flower (general):

*Size.*—130 to 150 mm.

*Borne.*—In axils of leaves, 1 per node.

*Form.*—Regular single.

*Life.*—One day.

*Blooming habit.*—Continuously, year round.

B. Corolla (petals):

*Color (general tonality from a distance of three meters).*—Bright red with satin glow.

*Color (upper surface).*—Closest to 40A. Eye: Basal part of eye closest to 46A, blending into 40A at 1/5 of the base of the petal.

*Color (under surface).*—Left ½ of underside of petal: 44C. Right ½: 19B overlaid with 19A with some red streaks.

C. Reproductive organs:

*Androecium (stamens).*—Numerous anthers, abundant pollen; color 15A.

*Gynoecium (pistil).*—Stigma: 5 in number, rounded, hairy. Color: 45A. Style: 42A, slightly darker at base.

PLANT

A. General appearance:

*Height.*—20 to 25 cm when grown as pot Hibiscus with 4 cuttings in a 15 cm pot and 1 to 2 applications of 400 ppm CCC.

*Branching pattern.*—Semi-upright.

B. Foliage:

*Color (upper surface).*—147A.

*Color (under surface).*—147B.

*Shape.*—See photograph.

I claim:

1. A new and distinct Hibiscus plant named Crimson Tide, as described and illustrated.

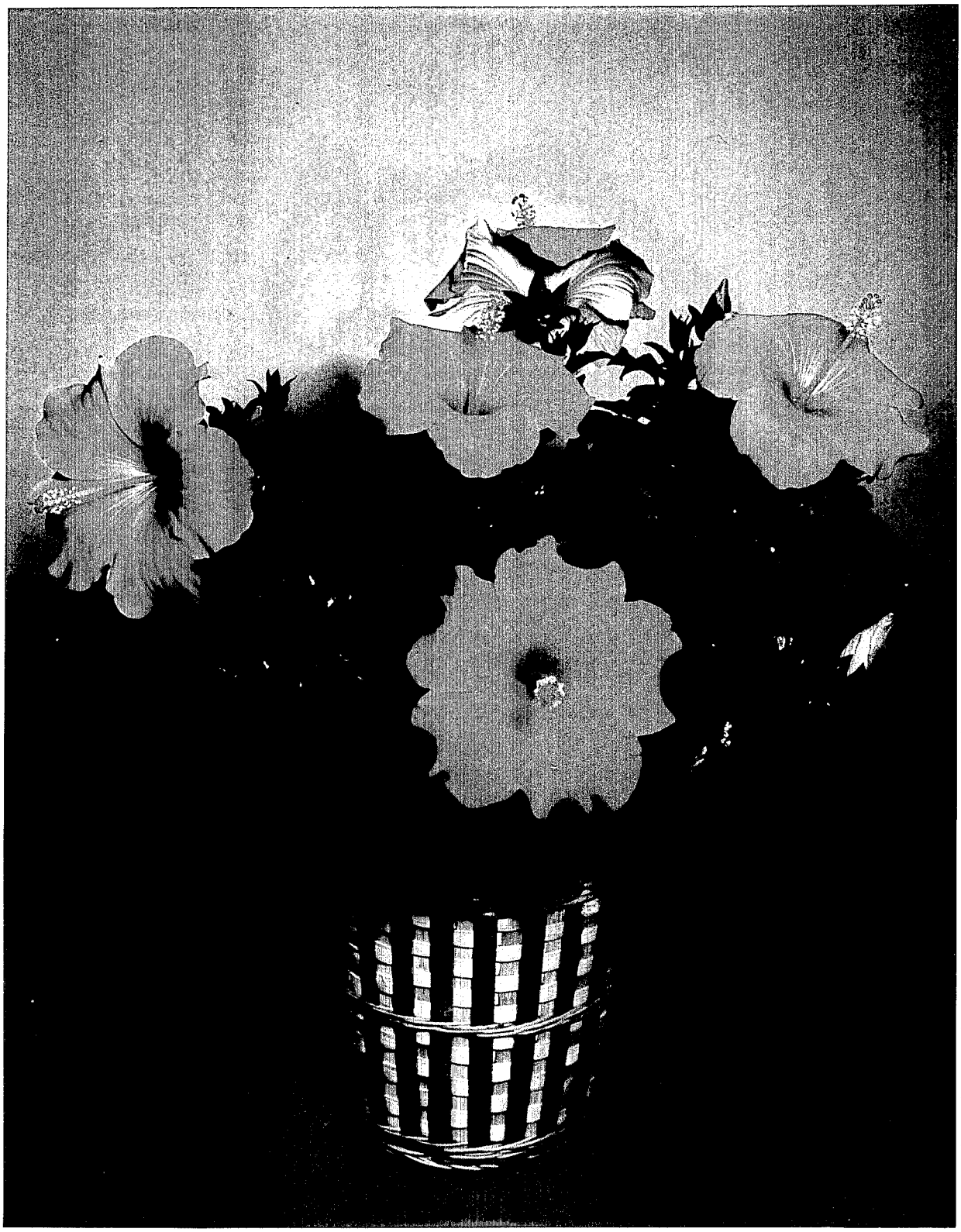

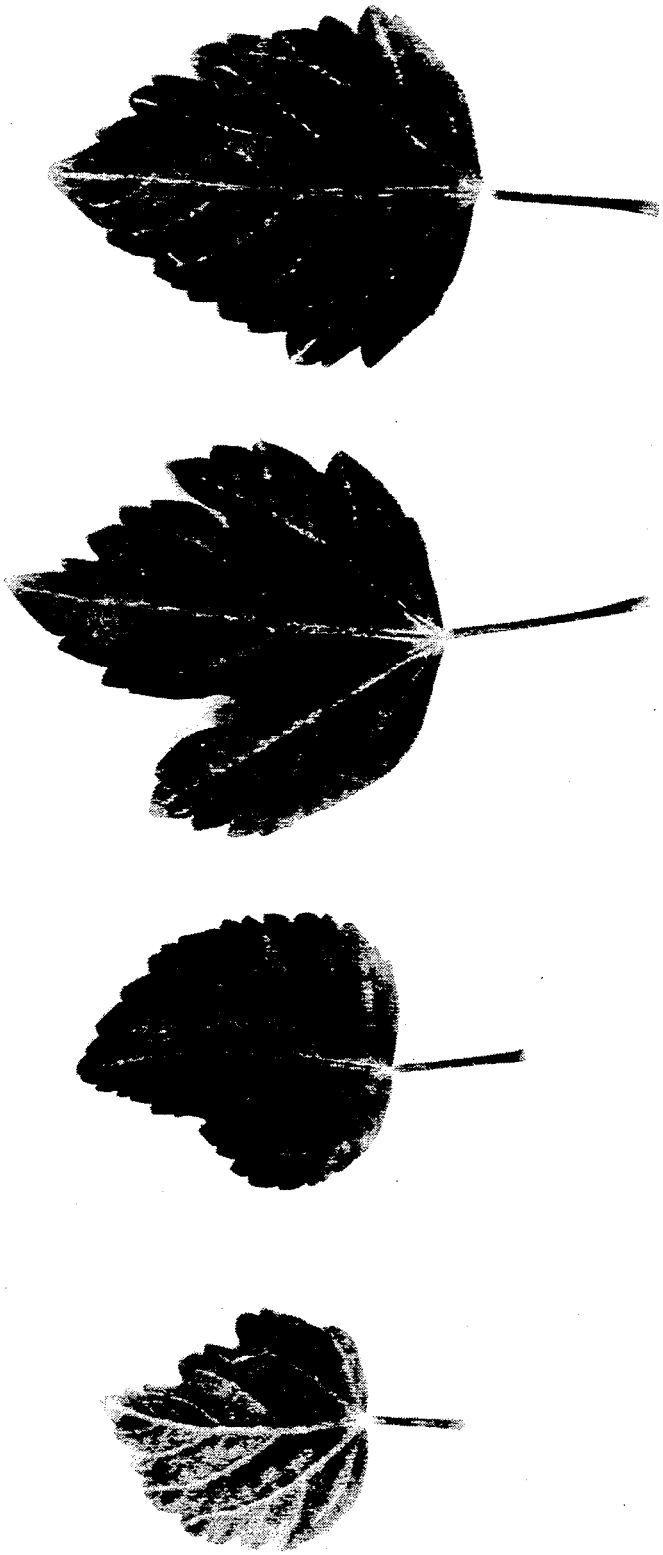

* * * * *